United States Patent [19]

Ohshika et al.

[11] Patent Number: 5,888,531
[45] Date of Patent: Mar. 30, 1999

[54] FREEZE-DRIED PREPARATION FOR PHARMACEUTICAL USE

[75] Inventors: Motoya Ohshika; Naoru Hamaguchi, both of Osaka; Shigehiro Higuchi, Hyogo, all of Japan

[73] Assignee: Takeda Chemical Industries, Ltd., Osaka, Japan

[21] Appl. No.: 677,046

[22] Filed: Jul. 1, 1996

[51] Int. Cl.$^6$ .............................. A61F 2/02; A61K 9/48; A61K 9/20; C07D 241/04

[52] U.S. Cl. ......................... 424/423; 424/451; 424/464; 544/384

[58] Field of Search .................... 424/423, 451, 424/464; 544/384

[56] References Cited

U.S. PATENT DOCUMENTS 5,084,480  1/1992  Pai et al. .................................. 514/554
5,294,713  3/1994  Sugihara et al. ........................ 544/384

FOREIGN PATENT DOCUMENTS

| 0383 680 | 2/1990 | European Pat. Off. . |
| 0438 747 | 12/1990 | European Pat. Off. . |
| 0529 858 | 8/1992 | European Pat. Off. . |
| 0 643 072 | 3/1995 | European Pat. Off. . |
| 0246 868 | 5/1997 | European Pat. Off. . |
| 42 42 863 | 12/1992 | Germany . |
| 96/33982 | 10/1996 | WIPO . |

*Primary Examiner*—Carlos A. Azpuru
*Attorney, Agent, or Firm*—Foley & Lardner

[57] ABSTRACT

A freeze-dried preparation comprising a bioactive substance having an optionally substituted amidino group and a disaccharide which stabilizes the bioactive substance; and a process for making the preparation are described.

14 Claims, No Drawings

FREEZE-DRIED PREPARATION FOR PHARMACEUTICAL USE

FIELD OF THE INVENTION

The present invention relates to a composition stably containing an essentially instable bioactive substance and is used in production of pharmaceuticals etc.

BACKGROUND OF THE INVENTION

With regard to traditionally known bioactive substances, some are relatively stable over time and others are instable. For example, compounds having an amidino group in their molecular structure are instable over time; there is demand for stable retention of such compounds.

SUMMARY OF THE INVENTION

Through extensive investigation aiming at resolving this problem, the present inventors found that the stability of compounds having an amidino group in their molecular structure can be improved by adding a disaccharide.

Accordingly, the present invention relates to a pharmaceutical composition containing both a bioactive substance having an optionally substituted amidino group and a disaccharide.

DETAILED DESCRIPTION OF THE INVENTION

Said bioactive substance having an optionally substituted amidino group (hereinafter simply referred to as bioactive substance) may be any one, as long as it has in its molecular structure 1 or more amidino groups that may be substituted. The optionally substituted amidino group is preferably substituted with an alkyl group. Said alkyl group is exemplified by alkyl groups having 1 to 4 carbon atoms, such as methyl, ethyl, propyl, isopropyl, butyl, isobutyl and tertiary butyl. The present invention is also applicable to compounds having an unsubstituted amidino group.

Specifically, the bioactive substance for the present invention is exemplified by:

(1) (S)-4-(trans-4-guanidinomethylcyclohexylcarbonylglycyl)-2-oxopiperazine-1,3-diacetic acid,
(2) (S)-4-(4-guanidinomethylbenzoylglycyl)-2-oxopiperazine-1,3-diacetic acid,
(3) (S)-4-(4-guanidinobenzoylglycyl)-2-oxopiperazine-1,3-diacetic acid,
(4) (S)-4-(4-guanidinobenzoylsarcosyl)-2-oxopiperazine-1,3-diacetic acid,
(5) (S)-4-(4-guanidinomethylbenzoylsarcosyl)-2-oxopiperazine-1,3-diacetic acid,
(6) (S)-1-carboxymethyl-4-(4-guanidinobenzoylsarcosyl)-2-oxopiperazine-3-propionic acid,
(7) (S)-4-(3-guanidinophenylacetylglycyl)-2-oxopiperazine-1,3-diacetic acid,
(8) (S)-4-(4-amidinobenzoylglycyl)-2-oxopiperazine-1,3-diacetic acid,
(9) 4-(4-amidinobenzoylglycyl)-2-oxopiperazine-1-acetic acid,
(10) (S)-4-(4-amidinobenzoylglycyl)-3-methoxycarbonylmethyl-2-oxopiperazine-1-acetic acid,
(11) (S)-4-(4-amidinobenzoylglycyl)-3-benzyl-2-oxopiperazine-1-acetic acid,
(12) (S)-4-(4-amidinobenzoylglycyl)-3-carbamoylmethyl-2-oxopiperazine-1-acetic acid,
(13) (S)-4-(4-amidinobenzoylglycyl)-1-carboxymethyl-2-oxopiperazine-3-propionic acid,
(14) 4-(4-amidinobenzoyl)aminoacetyl-3-[3-(4-amidinobenzoyl)aminopropyl]-2-oxopiperazine-1-acetic acid,
(15) 4-(4-amidinobenzoyl)aminoacetyl-3-[4-(4-amidinobenzoyl)aminobutyl]-2-oxopiperazine-1-acetic acid,
(16) 4-(4-amidinobenzoyl)aminoacetyl-3-[2-(4-amidinobenzoyl)aminoethyl]-2-oxopiperazine-1-acetic acid,
(17) 4-(4-amidinobenzoyl)aminoacetyl-3-[2-(4-amidinophenylaminocarbonyl)ethyl]-2-oxopiperazine-1-acetic acid,
(18) 4-(4-amidinobenzoyl)aminoacetyl-3-[3-(4-amidinophenylaminocarbonyl)propyl]-2-oxopiperazine-1-acetic acid,
(19) 4-(4-amidinobenzoyl)aminoacetyl-3-[4-(4-amidinophenylaminocarbonyl)butyl]-2-oxopiperazine-1-acetic acid,
(20) (S)-4-(4-guanidinobenzoylamino)acetyl-3-[3-(4-guanidinobenzoylamino)propyl]-2-oxopiperazine-1-acetic acid,
(21) (S)-4-(4-amidinobenzoylamino)acetyl-3-[2-(4-guanidinobenzoylamino)ethyl]-2-oxopiperazine-1-acetic acid,
(22) (S)-4-[4-(2-aminoethyl)benzoylamino]acetyl-3-[3-(4-amidinobenzoylamino)propyl]-2-oxopiperazine-1-acetic acid,
(23) (S,S)-3-[3-(4-guanidinobenzoylamino)propyl]-4-[3-(4-methoxyphenyl)-2-[4-(5-trifluoromethyl-[1,2,4]oxadiazol-3-yl-amino)benzoylamino]propionyl]-2-oxopiperazine-1-acetic acid,
(24) (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, and pharmaceutically acceptable esters or salts thereof. The optical isomens or racemate of these compound may be used as bioactive substance.

In addition to these compounds, there may be used antithrombotic compounds such as SB-207448, GR-200976, SC-58052, G-7453, G-7461, RO-43-5054, RO-43-8857, SC-52012, Fradafiban, SC-5684-A, SC-54701, GR-144053, DX-9065-A, FR-144633 and SB-208651; antibacterial compounds such as Coumamidine gamma-1 and Coumamidine gamma-2; antitumor compounds such as FCE-25217, CP-79328, CGP-48664, B-623, FCE-24561, tallimustine and distamycin-A; antirheumatic/antinephritic compounds such as TO-195; anti-inflammatory compounds such as BBE; antirheumatic/anti-asthmatic compounds such as CGS-25019-C; anti-angina pectoris/anti-myocardial infarction compounds such as lamifiban; anti-angina pectoris/anti-myocardial infarction/antithrombotic compounds such as SC-54684-A; anti-pancreatitis/anti-pulmonary edema/anti-esophagitis compounds such as sepimostat; antithrombotic/anti-protozoan compounds such as pentamidine isethionate; anti-depression compounds such as nitrafudam hydrochloride; antipancreatitic/anti-angina pectoris/antimyocardial infarction compounds such as nafamostat; anti-viral compounds such as ribamidine; and other compounds such as CGP-40215-A, diminazene, olmidine, propamidine, isometamidium, TAN-868-A, acetamide hydrochloride, amidinomycin, tapam, amicarbalide, dibrompropamidine, renyfoline hydrochloride, hexamidine, hydroxystilbamidine isethionate, isometamidium chloride and stilbamidine isethionate.

Pharmaceutically acceptable salts are normally salts with acids, e.g., salts with inorganic acids such as hydrochloric acid, hydrobromic acid, sulfuric acid, nitric acid and phosphoric acid, and salts with organic acids such as acetic acid, trifluoroacetic acid, tartaric acid, citric acid, fumaric acid, maleic acid, toluenesulfonic acid and methanesulfonic acid. For some compounds, however, their pharmacologically acceptable salts may be salts with bases, e.g., salts with alkali metals such as sodium and potassium, and salts with alkaline earth metals such as calcium and magnesium.

Non-peptide type compounds are preferable bioactive substance for use in the present invention.

The compounds (1) through (24) and the piperazin derivatives having a side chain including an amidino group at 3- or 4-position of the piperadin ring are also preferable.

A preferable embodiment of such piperazin derivatives is a compound of the formula (I):

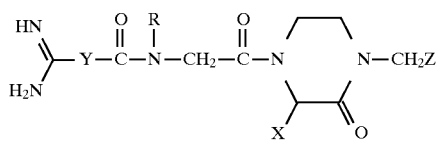

wherein R represents a hydrogen atom or an alkyl group, x represents a hydrogen atom or an optionally substituted alkyl group, Y represents a cyclic hydrocarbon group which may be bound through 1 or 2 atoms and Z represents an optionally amidated or esterified carboxyl group, or a pharmaceutically acceptable salt thereof.

In the above formula (I), the alkyl group represented by R is a $C_{1-6}$ alkyl group, such as methyl, ethyl, propyl, isopropyl, butyl, sec-butyl, tert-butyl, pentyl or hexyl, preferably a $C_{1-4}$ alkyl group.

The optionally substituted alkyl group represented by X includes a $C_{1-4}$ straight chain alkyl group (ex. methyl, ethyl, propyl, butyl) which may be substituted with, for example an optionally amidated or esterified carboxyl group ($C_{1-4}$ alkylester such as methylester or ethylester), phenyl or a group of formula: A—B—D, wherein A is an amino, amidino or guanidine group, B is a phenylene group, and D is —CONH— (either of the bonds of D may be bound to B).

The cyclic hydro-carbon group which may be bound through 1 or 2 atoms represented by Y includes a saturated or unsaturated 5 or 6 membered cyclic hydrocarbon group which may be bound through carbon or nitrogen atoms, and includes cyclopentan, cyclohexan, phenyl or the like, which may be bound through an imino or methylen group for instance.

The esterified carboxyl group represented by Z is a $C_{1-4}$ alkylester such as methylester or ethylester.

The compound of the above formula (I) includes R-configurated ones and S-configurated ones, when the compound has an asymmetric carbon in the molecule.

Compounds (1) through (13) above are described in Japanese Patent Unexamined Publication No. 25285/1994, the contents of which are incorporated herein by reference in their entirely; compounds (14) through (24) above can, for example, be produced by the methods described in Reference Examples below.

The compound of the above formula (I) may be produced in a similar way of them.

The disaccharide for the present invention may be of the maltose type, exemplified by maltose, cellobiose, gentiobiose, melibiose, lactose, turanose and sorbose, or the trehalose type, exemplified by trehalose, isotrehalose, sucrose and isosaccharose. Of these disaccharides, sucrose, lactose and maltose are preferred, with greater preference given to sucrose. These disaccharides may be used singly or in mixture of 2 or more kinds.

The pharmaceutical composition of the present invention comprises a bioactive substance and a disaccharide, their content ratio being from about 1 to about 1,000, preferably from about 5 to about 500 parts by weight of disaccharide to 1 part by weight of bioactive substance.

The freeze-dried preparation of the present invention is preferably made solid by freeze-drying an aqueous solutions of both a bioactive substance and a disaccharide in water or an aqueous solvent (e.g., water-alcohol mixture). Said aqueous solution can easily be prepared as a sterile preparation by filtration through a 0.22 μm filter, for instance. The freeze-dried preparation of the present invention is stable and is capable of long suppressing the degradation and deterioration of the bioactive compound, for example for one month.

A method of producing the freeze-dried preparation of the present invention in detail is hereinafter described.

To obtain an aqueous solution, both a bioactive substance and a disaccharide may be dissolved in water or an aqueous solvent by a commonly known method. It does not matter which component to dissolve first.

The above aqueous solution of bioactive substance and disaccharide may be supplemented with an isotonizing agent to adjust osmotic pressure. Said isotonizing agent is exemplified by commonly known isotonizing agents, e.g., monosaccharides such as glucose, sugar alcohols such as mannitol, and salts such as sodium chloride.

The freeze-dried preparation of the present invention can normally be obtained by first dissolving both a bioactive substance and a disaccharide in water or an aqueous solvent, then freeze-drying the resulting aqueous solution by a commonly known method. More specifically, the aqueous solution as prepared above is frozen, preferably at a temperature below the eutectic point, after which the drying chamber is kept under vacuum conditions while the rack temperature is gradually increased to a primary drying temperature and drying at the temperature. Upon completion of the primary drying, the rack temperature is further increased to a secondary drying temperature, followed by secondary drying. Rack temperature may be constant between primary and secondary drying processes. The bioactive substance concentration in the aqueous solution is usually from about 0.01 to about 500 mg/ml, the disaccharide concentration being normally from about 0.01 to about 1,000 mg/ml.

The freeze-dried preparation for pharmaceutical use of the present invention can usually be used orally or non-orally as a pharmaceutical composition, and may comprise a pharmacologically acceptable carrier or excipient.

The freeze-dried preparation of the present invention can be tableted into tablet preparations, and can be filled in capsules to yield capsule preparations. It can also be used as an injectable preparation, including intravenous, subcutaneous, intramuscular or drip infusion injection, or an ophthalmic solution. It may be dissolved in water for injection or in a transfusion solution (e.g., physiological saline, glucose solution). This solution of the preparation of the present invention in water for injection or a nutrient solution is sufficiently stable to achieve the goal of the invention. The bioactive substance concentration is usually from about 0.01 to about 10 mg/ml. The disaccharide concentration is normally from about 0.01 to about 1,000 mg/ml.

An injectable preparation which may be dissolved before use is preferably prepared by a commonly known method of sterilization such as filtering sterilization. Also, the disaccharide or a mixture of the disaccharide and other additives may be previously treated to remove pyrogens before being used in the preparation.

The freeze-dried preparation of the present invention is used against target diseases corresponding to the drug effect of the bioactive substance used.

The pharmaceutical composition of the present invention containing one of compounds (1) through (24) above as a bioactive substance exhibits antiplatelet action in mammals (e.g., mice, rats, rabbits, cats, dogs, bovines, goats, monkeys, humans), is low in toxicity and safe to humans and livestock, and can be used orally or non-orally as a therapeutic agent for cerebral thrombosis (acute phase), transient cerebral ischemic attack and instable angina pectoris in mammals, including humans. In such cases, dose volume varies depending on dosage form, method of administration, type of active ingredient used, and other factors. For example, when the pharmaceutical composition of the present invention is intravenously administered as an aqueous solution, it is administered at such dose volumes that about 0.1 to about 10 mg of the antiplatelet bioactive substance is administered per human adult per day. Said composition may be administered once or 2 to 3 times per day. It can also be used as a instillation. Transfusion solutions which can be used for this drip infusion include physiological saline and 5% glucose solution. In this case, the pharmaceutical composition of the present invention can also be used in a kit with a transfusion solution. It can also be used as a high value-added preparation such as a prefilled syringe preparation or DPS (dual chamber prefilled syringe) preparation. When an aqueous solution of an injectable preparation etc. is prepared, it is preferable that the liquid be previously rendered weakly acidic to weakly alkaline. For this purpose, weakly acidic to weakly alkaline pH can be obtained using an inorganic acid such as hydrochloric acid, hydrobromic acid, sulfuric acid, nitric acid or phosphoric acid, an organic acid such as acetic acid, tartaric acid, citric acid, fumaric acid, maleic acid, toluenesulfonic acid or methanesulfonic acid, or a sodium salt thereof.

EXAMPLES

The present invention is hereinafter described in more detail by means of the following examples, however, the scope of the present invention should not be limited by them.

Example 1

Freeze-dried preparations containing (S)-4-(4-amidinobenzoylglycyl)-3-methoxycarbonylmethyl-2-oxopiperazine-1-acetic acid hydrochloride (compound A) and a sugar (mannitol, sucrose, lactose, or maltose) in the respective ratios shown in Table 1 were prepared and subjected to an accelerated stability test; the results shown in Table 2 were obtained. Formula A (using mannitol) is a comarison composition. Formula B,C and D (using disaccharides) are composition of the present invention. Lyophilization was achieved by dissolving 0.2% compound A and 2% of sugar in water, freezing the aqueous solution at about −40° C., then increasing the rack temperature to 30° C. at a rate of about 7.5° C./hr, while maintaining a vacuum of under about 0.1 torr in the drying chamber, and drying at constant temperature for at least 10 hours.

TABLE 1

Compositions of Formulas A through D

| | Formula A | Formula B | Formula C | Formula D |
|---|---|---|---|---|
| compound A | 2 mg | 2 mg | 2 mg | 2 mg |
| Mannitol | 20 mg | — | — | — |
| Sucrose | — | 20 mg | — | — |
| Lactose | — | — | 20 mg | — |
| Maltose | — | — | — | 20 mg |

TABLE 2

Stability Test Results for Formulas A through D

| Conditions | Formula A | Formula B | Formula C | Formula D |
|---|---|---|---|---|
| INT | 100.0% | 100.0% | 100.0% | 100.0% |
| 40° C. · 1M | 97.5% | 99.9% | 99.3% | 99.9% |
| 50° C. · 1M | 96.3% | 99.4% | 100.0% | 101.9% |
| 60° C. · 2W | 95.1% | 99.0% | 100.5% | 99.8% |
| 60° C. · 1M | 93.5% | 100.0% | 100.3% | 95.9% |

Formulas B, C and D, all based on the pharmaceutical composition of the present invention, surpassed the comparison composition, formula A, in terms of stability for 1 month at all temperatures tested.

Example 2

The freeze-dried preparation containing 0.5 mg of (S)-4-(4-amidinobenzoylglycyl)-3-methoxycarbonylmethyl-2-oxopiperazine-1-acetic acid (compound A) and 5 mg of sucrose were prepared. The preparation was prepared by freeze-drying a solution containing 0.05% compound A and 0.5% sucrose according to the same method as described in Example 1.

The appearance of the thus obtained preparation is white block, and the preparation is dissolved in distilled water to give a colorless and transparent solution.

Example 3

The freeze-dried preparation containing 2 mg of (S)-4-(4-guamidinobenzoylaminoacetyl-3-[3-(4-guanidinobenzoyl)amino]propyl-2-oxopiperazine-1-acetic acid (compound B) and 20 mg of sucrose. The preparation was obtained by freeze-drying the solution containing 0.2% compound B and 2% sucrose according to the method as described in Example 1.

The appearance of thus obtained preparation is white block, and the preparation is dissolved in the distilled water to give a colorless and transparent solution.

The following examples illustrate how to make bioactive compounds useful in the present invention.

Reference Example 1

(S)-3-(3-tert-butoxycarbonylaminopropyl)-2-oxopiperazine-1-acetic acid tert-butyl ester oxalate (2,2-dimethoxyethyl)aminoacetic acid tert-butyl ester (6.0 g, 27.7 mmol) and N-Z-Orn(Boc)—OH (10.0 g, 27.7 mmol) were dissolved in 54.6 ml of acetone; under stirring at 15° C., 1-ethyl-3-(3-dimethylaminopropyl)-carbodiimide hydrochloride (5.6 g, 29.2 mmol) was added. After being stirred at room temperature for 1 hour, the reaction mixture was concentrated under reduced pressure; the residue was dissolved in ethyl acetate and washed with 5% aqueous potassium hydrogen sulfate and saturated aqueous sodium bicarbonate. The organic layer was concentrated under reduced pressure to yield a light-yellow oily substance. This oily substance and p-toluenesulfonic acid 1.0 hydrate (1.04 g, 5.46 mmol) were dissolved in 137 ml of toluene, followed by stirring at 70° C. for 2 hours. The reaction mixture was poured over saturated aqueous sodium bicarbonate and extracted with ethyl acetate for liquid phase separation. The organic layer was concentrated under reduced pressure and purified by silica gel column chromatography (hexane/ethyl acetate=3/2) to yield 8.3 g of a light-yellow oily substance. This oily substance (8.3 g, 16.5 mmol) was dissolved in 166 ml of ethyl acetate; 1.7 g of 10% Pd—C was added, followed by stirring in a hydrogen atmosphere for 2 hours. After the catalyst was filtered off, the filtrate was concentrated under reduced pressure. The residue was dissolved in 16.6 ml of methanol; oxalic acid 2.0 hydrate (2.1 g, 16.5 mmol) was added, followed by concentration under reduced pressure. The resulting crystal was washed with ethyl acetate to yield 5.1 g (66.8%) of the title compound as a white crystal.
Optical rotation: $[\alpha]_D$ −29.3° (C=0.73, $H_2O$)
Melting point: 181° C.
Elemental analysis (for $C_{18}H_{33}N_3O_5 \cdot (CO_2H)_2$ (465.511)):
Calculated: C, 52.05; H, 7.64; N, 9.10
Found: C, 51.98; H, 7.61; N, 9.20

Reference Example 2
(S)-4-benzyloxycarbonylaminoacetyl-3-(3-tert-butoxycarbonylaminopropyl)-2-oxopiperazine-1-acetic acid tert-butyl ester (S)-3-(3-tert-butoxycarbonylaminopropyl)-2-oxopiperazine-1-acetic acid tert-butyl ester oxalate (1.6 g, 3.47 mmol) was dissolved in saturated aqueous sodium bicarbonate and extracted with ethyl acetate for liquid phase separation, followed by concentration under reduced pressure. The residue and N-Z-Gly—OH (0.87 g, 4.16 mmol) were dissolved in 16.0 ml of acetone; under stirring at 15° C., 1-ethyl-3-(3-dimethylaminopropyl)-carbodiimide hydrochloride (0.87 g, 4.51 mmol) was added. After being stirred at room temperature for 1 hour, the reaction mixture was concentrated under reduced pressure; the residue was dissolved in ethyl acetate and washed with 5% aqueous potassium hydrogen sulfate and saturated aqueous sodium bicarbonate. The organic layer was concentrated under reduced pressure; the residue was purified by silica gel column chromatography (ethyl acetate) to yield 1.95 g (100%) of the title compound as a colorless amorphous powder.
IR ν max $cm^{-1}$: 3360, 2970, 2930, 1713, 1650, 1513, 1448, 1363, 1246, 1158, 1045, 964, 848, 744, 695; NMR ($CDCl_3$) δ: 1.43 (9H, s), 1.46 (9H, s), 1.50–2.20 (4H, m), 3.02–4.28 (10H, m), 4.52–4.80 (1H, m), 5.01 (1H, dd, J=8.8 Hz, J=4.6 Hz), 5.13 (2H, s), 5.64–5.86 (1H, m), 7.37 (5H, s)

Reference Example 3
(S)-4-(4-amidinobenzoyl)aminoacetyl-3-(3-aminopropyl)-2-oxopiperazine-1-acetic acid trifluoroacetate (S)-4-benzyloxycarbonylaminoacetyl-3-(3-tert-butoxycarbonylaminopropyl)-2-oxopiperazine-1-acetic acid tert-butyl ester (1.34 g, 2.38 mmol) was dissolved in 13.4 ml of methanol; 0.54 g of 10% Pd-C was added, followed by stirring in a hydrogen atmosphere for 30 minutes. After the catalyst was filtered off, the filtrate was concentrated under reduced pressure. The residue and sodium bicarbonate (0.4 g, 4.76 mmol) were dissolved in 26.8 ml of $H_2O$ and 13.4 ml of 1,4-dioxane; under stirring at room temperature, 4-amidinobenzoyl chloride hydrochloride (0.68 g, 3.09 mmol) was added. After being stirred for 3 hours, the reaction mixture was adjusted to pH 4 with 1N aqueous hydrochloric acid and concentrated to dryness. The residue was dissolved in 3.75 ml of trifluoroacetic acid and stirred at room temperature for 2 hours. The reaction mixture was concentrated under reduced pressure and purified by CHP-20 (Mitsubishi Kasei) column chromatography ($H_2O$) to yield 1.0 g (63.3%) of the title compound as a colorless amorphous powder.
Optical rotation: $[\alpha]_D$ +35.4° (C=0.75, MeOH)
Elemental analysis (for $C_{19}H_{26}N_6O_5 \cdot 2CF_3CO_2H \cdot H_2O$ (664.515)):
Calculated: C, 41.57; H, 4.55; N, 12.65
Found: C, 41.86; H, 4.50; N, 12.60

Reference Example 4
(S)-4-(4-amidinobenzoyl)aminoacetyl-3-{3-(4-amidinobenzoyl)amino}propyl-2-oxopiperazine-1-acetic acid trifluoroacetate (S)-4-(4-amidinobenzoylamino)acetyl-3-(3-aminopropyl)-2-oxopiperazine-1-acetic acid trifluoroacetate (0.5 g, 0.94 mmol) and sodium bicarbonate (0.32 g, 3.76 mmol) were dissolved in 5.0 ml of $H_2O$ and 2.5 ml of 1,4-dioxane; under stirring at room temperature, 4-amidinobenzoyl chloride hydrochloride (0.22 g, 0.99 mmol) was added. After being stirred for 2 hours, the reaction mixture was adjusted to pH 4 with 1N aqueous HCl and concentrated under reduced pressure. The residue was purified by CHP-20 column chromatography ($H_2O \rightarrow 5\%$ $CH_3CN$) to yield 0.34 g (50.7%) of the title compound as a colorless amorphous powder.
Optical rotation: $[\alpha]_D$ +41.90° (C=0.73, MeOH)
Elemental analysis (for $C_{27}H_{32}N_8O_6 \cdot CF_3CO_2H \cdot 2H_2O$ (714.653)):
Calculated: C, 48.74; H, 5.22; N, 15.68
Found: C, 48.52; H, 5.22; N, 15.57

Reference Example 5
(S)-3-(4-tert-butoxycarbonylaminobutyl)-2-oxopiperazine-1-acetic acid tert-butyl ester oxalate The title compound was synthesized in the same manner as in Reference Example 1 using N-Z-Lys(Boc)—OH.
Optical rotation: $[\alpha]_D$ −29.0° (C=1.02, DMSO)
Melting point: 170°–172° C.
Elemental analysis (for $C_{19}H_{35}N_3O_5 \cdot (CO_2H)_2$ (475.540)):
Calculated; C, 53.04; H, 7.84; N, 8.84
Found : C, 52.75; H, 7.65; N, 8.66

Reference Example 6
(S)-4-benzyloxycarbonylaminoacetyl-3-(4-tert-butoxycarbonylaminobutyl)-2-oxopiperazine-1-acetic acid tert-butyl ester The title compound was synthesized in the same manner as in Reference Example 2 using (S)-3-(4-tert-butoxycarbonylaminobutyl)-2-oxopiperazine-1-acetic acid tert-butyl ester oxalate.
IR ν max $cm^{-1}$: 3400, 2990, 2945, 1713, 1657, 1520, 1458, 1368, 1253, 1166, 1070, 745, 700; NMR ($CDCl_3$) δ: 1.42 (9H, s), 1.46 (9H, s), 1.18–2.12 (6H, m), 2.92–4.28 (10H, m), 4.48–4.84 (1H, m), 5.02 (1H, dd, J=8.6 Hz, J=4.8 Hz), 5.13 (2H, s), 5.60–5.88 (1H, m), 7.36 (5H, s)

Reference Example 7
(S)-4-(4-amidinobenzoylamino)acetyl-3-(4-aminobutyl)-2-oxopiperazine-1-acetic acid trifluoroacetate The title compound was synthesized in the same manner as in Reference Example 3 using (S)-[4-benzyloxycarbonylaminoacetyl-3-(4-tert-butoxycarbonylamino-butyl)-2-oxopiperazin-1-yl]-acetic acid tert-butyl ester.
Optical rotation: $[\alpha]_D$ +46.8° (C=1.01, $H_2O$)
Elemental analysis (for $C_{20}H_{28}N_6O_5 \cdot 1.7CF_3CO_2H \cdot 2H_2O$ (662.394)):
Calculated: C, 42.43; H, 5.13; N, 12.69
Found: C, 42.53; H, 4.88; N, 12.78

Reference Example 8
(S)-4-(4-amidinobenzoylamino)acetyl-3-{4-(4-amidinobenzoylamino)butyl}-2-oxopiperazine-1-acetic acid monotrifluoroacetate monohydrate The title compound was synthesized in the same manner as in Reference Example 4 using (S)-4-(4- amidinobenzoylamino)acetyl- 3-(4-aminobutyl)-2-oxopiperazine-1-acetic acid trifluoroacetate.
Optical rotation: $[\alpha]_D$ +44.3° (C=1.01, $H_2O$)
Elemental analysis (for $C_{28}H_{34}N_8O_6 \cdot CF_3CO_2H \cdot HCl3H_2O$ (783.157)):
Calculated: C, 46.01; H, 5.41; N, 14.31
Found: C, 46.23; H, 5.22; N, 14.54

Reference Example 9
(S,S)-4-{2-benzyloxycarbonylamino-3-(4-methoxyphenyl) propionyl}-3-(3-tert-butoxycarbonylaminopropyl)-2-oxopiperazine-1-acetic acid tert-butyl ester The title compound was synthesized in the same manner as in Reference Example 2 using N-Z-Tyr(OMe)—OH.
IR $\nu$ max $cm^{-1}$: 3360, 2975, 2925, 1710, 1643, 1512, 1448, 1360, 1245, 1152, 1033, 743, 696; NMR ($CDCl_3$) $\delta$: 1.41 (9H, s), 1.44 (9H, s), 1.30–2.10 (3H, m), 2.20–2.44 (1H, m), 2.80–3.84 (10H, m), 3.77 (3H, s), 4.23 (1H, d, J=17.2 Hz), 4.50–4.85 (1H, m), 4.93 (1H, dd, J=6.2 Hz, J=7.0 Hz), 5.09 (2H, dd, J=12.0 Hz, J=16.4 Hz), 5.67 (1H, d, J=8.8 Hz), 6.80 (2H, d, J=8.8 Hz), 7.09 (2H, d, J=8.8 Hz), 7.35 (5H, s)

Reference Example 10
(S,S)-4-{2-(4-amidinobenzoylamino)-3-(4-methoxyphenyl)-propionyl}-3-(3-aminopropyl)-2-oxopiperazine-1-acetic acid trifluoroacetate The title compound was synthesized in the same manner as in Reference Example 3 using (S,S)-4-{2-benzyloxycarbonylamino-3-(4-methoxyphenyl)propionyl}-3-(3-tert-butoxycarbonylaminopropyl)-2-oxopiperazine-1-acetic acid tertbutyl ester.
Optical rotation: $[\alpha]_D$ +78.2° (C=0.62, $H_2O$)
Elemental analysis (for $C_{27}H_{34}N_6O_6 \cdot CF_3CO_2H \cdot 3H_2O$ (706.672)):
Calculated: C, 49.29; H, 5.85; N, 11.89
Found: C, 49.53; H, 5.68; N, 11.90

Reference Example 11
(S,S)-4-{2-(4-amidinobenzoylamino)-3-(4-methoxyphenyl)-propionyl}-3-{3-(4-amidinobenzoylamino)propyl}-2-oxopiperazine-1-acetic acid trifluoroacetate The title compound was synthesized in the same manner as in Reference Example 4 using (S,S)-4-{2-(4-amidinobenzoylamino)-3-(4-methoxyphenyl)propionyl}-3-(3-aminopropyl)-2-oxopiperazine-1-acetic acid trifluoroacetate.
Optical rotation: $[\alpha]_D$ +52.8° (C=0.76, MeOH)
Elemental analysis (for $C_{35}H_{40}N_8O_7 \cdot CF_3CO_2H \cdot 3H_2O$ (852.820)):
Calculated: C, 52.11; H, 5.55; N, 13.14
Found: C, 52.27; H, 5.50; N, 13.26

Reference Example 12
(S,S)-4-{2-benzyloxycarbonylamino-3-(4-methoxyphenyl)-propionyl}-3-(4-tert-butoxycarbonylaminobutyl)-2-oxopiperazine-1-acetic acid tert-butyl ester The title compound was synthesized in the same manner as in Reference Example 2 using (S)-3-(4-tert-butoxycarbonylaminobutyl)-2-oxopiperazine-1-acetic acid tert-butyl ester oxalate and N-Z-Tyr(OMe)—OH.
IR $\nu$ max $cm^{-1}$: 3345, 2975, 2930, 1712, 1646, 1512, 1447, 1364, 1244, 1155, 1034, 743, 696; NMR ($CDCl_3$) $\delta$: 1.43 (9H, s), 1.44 (9H, s), 1.00–2.45 (6H, m), 2.80–3.90 (10H, m), 3.78 (3H, s), 4.23 (1H, d, J=17.4 Hz), 4.70–5.10 (2H, m), 5.10 (2H, d, J=2.4 Hz), 5.74 (1H, d, J=8.8 Hz), 6.81 (2H, d, J=8.6 Hz), 7.10 (2H, d, J=8.6 Hz), 7.35 (5H, s)

Reference Example 13
(S,S)-4-{2-(4-amidinobenzoylamino)-3-(4-methoxyphenyl) propionyl}-3-(4-aminobutyl)-2-oxopiperazine-1-acetic acid trifluoroacetate The title compound was synthesized in the same manner as in Reference Example 3 using (S,S)-[4-{2-benzyloxycarbonylamino- 3-(4-methoxyphenyl)-propionyl}-3-(4-tert-butoxycarbonylaminobutyl)-2-oxopiperazine-1-yl]-acetic acid tert-butyl ester.
Optical rotation: $[\alpha]_D$ +53.1° (C=0.64, MeOH)
Elemental analysis (for $C_{28}H_{36}N_6O_6 \cdot CF_3CO_2H \cdot 3H_2O$ (720.699)):
Calculated: C, 50.00; H, 6.01; N, 11.66
Found: C, 49.87; H, 5.77; N, 11.45

Reference Example 14
(S,S)-4-{2-(4-amidinobenzoylamino)-3-(4-methoxyphenyl) propionyl}-3-{4-(4-amidinobenzoylamino)butyl}-2-oxopiperazine-1-acetic acid hydrochloride The title compound was synthesized in the same manner as in Reference Example 4 using (S,S)-4-{2-(4-amidinobenzoylamino)-3-(4-methoxyphenyl)propionyl}-3-(4-aminobutyl)-2-oxopiperazine-1-acetic acid trifluoroacetate.
Optical rotation: $[\alpha]_D$ +54.5° (C=0.88, $H_2O$)
Elemental analysis (for $C_{36}H_{42}N_8O_7 \cdot HCl \cdot 6H_2O$ (843.329)):
Calculated: C, 51.27; H, 6.57; N, 13.29
Found: C, 51.24; H, 6.37; N, 13.26

Reference Example 15
(S)-4-benzyloxycarbonylaminoacetyl-3-{3-(6-tert-butoxycarbonylaminohexanoylamino)propyl}-2-oxopiperazine-1-acetic acid (S)-4-benzyloxycarbonylaminoacetyl-3-(3-tert-butoxycarbonylaminopropyl)-2-oxopiperazine-1-acetic acid tert-butyl ester as obtained in Reference Example 2 (0.6 g, 1.07 mmol) was dissolved in 3.0 ml of trifluoroacetic acid, followed by stirring at room temperature for 30 minutes, after which the reaction mixture was concentrated under reduced pressure. Separately, 6-tert-butoxyaminocaproic acid (0.26 g, 1.12 mmol), 1-ethyl-3-(3-dimethylaminopropyl)-carbodiimide hydrochloride (0.22 g, 1.14 mmol) and 1-hydroxybenzotriazole (0.15 g, 1.12 mmol) were dissolved in 2.1 ml of DMF, followed by stirring for 1 hour. To this solution, of the above residue and 2.1 ml of a DMF solution comprising triethylamine (0.3 ml, 2.14 mmol) was added, followed by stirring at room temperature for 4 hours. The reaction mixture was diluted with ethyl acetate and washed with 5% aqueous potassium hydrogen sulfate and saturated aqueous sodium bicarbonate. The organic layer was concentrated under reduced pressure; the residue was purified by silica gel column chromatography (ethyl acetate/methanol/acetic acid=20/10/0.6) to yield 0.42 g (63.3%) of the title compound as a colorless amorphous powder.
IR $\nu$ max $cm^{-1}$: 3320, 2930, 1643, 1533, 1448, 1203, 1173, 1046; NMR ($CDCl_3$) $\delta$: 1.42 (9H, s), 1.20–2.09 (10H, m), 2.17 (2H, t, J=7.3 Hz), 2.92–4.20 (12H, m), 4.80–4.98 (1H, m), 5.11 (2H, s), 7.22–7.44 (5H, m)

Reference Example 16
(S)-4-(4-amidinobenzoylamino)acetyl-3-{3-(6-aminohexanoyl-amino)propyl}-2-oxopiperazine-1-acetic acid trifluoroacetate (S)-4-benzyloxycarbonylaminoacetyl-3-(3-(6-tert-butoxycarbonylaminohexanoylamino)propyl)-2-oxopiperazine-1-acetic acid (0.42 g, 0.68 mmol) was dissolved in 8.4 ml of methanol; 0.17 g of 10% Pd-C was added, followed by stirring in a hydrogen atmosphere for 1 hour. After the catalyst was filtered off, the filtrate was concentrated under reduced pressure. The residue and sodium bicarbonate (0.18 g, 2.14 mmol) were dissolved in 8.4 ml of H₂O and 4.2 ml of 1,4-dioxane; under stirring at room temperature, 4-amidinobenzoyl chloride hydrochloride (0.20 g, 0.93 mmol) was added. After being stirred for 1 hour, the reaction mixture was adjusted to pH 4 with 1N aqueous HCl and concentrated to dryness. The residue was dissolved in 4.3 ml of trifluoroacetic acid and stirred at room temperature for 1 hour. The reaction mixture was concentrated under reduced pressure; the residue was purified by CHP-20 column chromatography (H₂O→5% CH₃CN) to yield 0.26 g (55%) of the title compound as a colorless amorphous powder.

Optical rotation: $[\alpha]_D$ +42.7° (C=0.99, MeOH)
Elemental analysis (for $C_{25}H_{37}N_7O_6 \cdot 1.1CF_3CO_2H \cdot 2H_2O$ (693.067)):
Calculated: C, 47.14; H, 6.12; N, 14.15
Found: C, 47.30; H, 5.82; N, 14.40

Reference Example 17

(S)-4-benzyloxycarbonylaminoacetyl-3-{3-(5-tert-butoxycarbonylaminopentanoylamino)propyl}-2-oxopiperazine-1-acetic acid The title compound was synthesized in the same manner as in Reference Example 15 using 5-tert-butoxyaminovaleric acid.

IR ν max cm⁻¹: 3370, 2940, 1650, 1533, 1455, 1254, 1170, 1050; NMR (CDCl₃) δ: 1.42 (9H, s), 1.28–2.08 (8H, m), 2.18 (2H, t, J=7.0 Hz), 3.03 (2H, t, J=6.8 Hz), 3.10–4.20 (10H, m), 4.82–5.00 (1H, m), 5.11 (2H, s), 7.22–7.52 (5H, m)

Reference Example 18

(S)-4-(4-amidinobenzoylamino)acetyl-3-{3-(5-aminopentanoylamino)propyl}-2-oxopiperazine-1-acetic acid trifluoroacetate The title compound was synthesized in the same manner as in Reference Example 16 using (S)-4-benzyloxycarbonylaminoacetyl-3-{3-(5-tert-butoxycarbonylaminopentanoylamino)propyl}-2-oxopiperazin-1-acetic acid.

Optical rotation: $[\alpha]_D$ +46.0° (C=1.01, MeOH)
Elemental analysis (for $C_{24}H_{35}N_7O_6 \cdot CF_3CO_2H \cdot 2.5H_2O$ (676.646)):
Calculated: C, 46.15; H, 6.11; N, 14.49
Found: C, 46.43; H, 6.15; N, 14.20

Reference Example 19

(S)-4-benzyloxycarbonylaminoacetyl-3-{3-(4-tert-butoxycarbonylaminobutanoylamino)propyl}-2-oxopiperazine-1-acetic acid The title compound was synthesized in the same manner as in Reference Example 15 using 4-tert-butoxyaminobutyric acid.

IR ν max cm⁻¹: 3350, 2930, 1642, 1530, 1452, 1252, 1170, 1050; NMR (CDCl₃) δ: 1.42 (9H, s), 1.30–2.10 (4H, m), 1.73 (2H, t, J=7.2 Hz), 2.18 (2H, t, J=7.5 Hz), 3.04 (2H, t, J=6.8 Hz), 3.10–4.20 (10H, m), 4.83–4.97 (1H, m), 5.11 (2H, s), 7.22–7.50 (5H, m)

Reference Example 20

(S)-4-(4-amidinobenzoylamino)acetyl-3-{3-(4-aminobutanoylamino)propyl}-2-oxopiperazine-1-acetic acid trifluoroacetate The title compound was synthesized in the same manner as in Reference Example 16 using (S)-4-benzyloxycarbonylaminoacetyl-3-{3-(4-tert-butoxycarbonylaminobutanoylamino)-propyl}-2-oxopiperazine-1-acetic acid.

Optical rotation: $[\alpha]_D$ +47.9° (C=1.00, H₂O)

Elemental analysis (for $C_{23}H_{33}N_7O_6 \cdot 1.5CF_3CO_2H \cdot 2H_2O$ (710.623)):
Calculated: C, 43.95; H, 5.46; N, 13.80
Found: C, 44.23; H, 5.63; N, 13.52

Reference Example 21

(S,S)-4-{2-(4-amidinobenzoylamino)-3-(4-methoxyphenyl)propionyl}-3-(4-guanidinobutyl)-2-oxopiperazine-1-acetic acid hydrochloride (S,S)-4-{2-benzyloxycarbonylamino-3-(4-methoxyphenyl)propionyl}-3-(4-tert-butoxycarbonylaminobutyl)-2-oxopiperazine-1-acetic acid tert-butyl ester as obtained in Reference Example 12 (0.6 g, 0.86 mmol) was dissolved in 2.0 ml of trifluoroacetic acid, followed by stirring at room temperature for 1 hour, after which the reaction mixture was concentrated under reduced pressure. 5.6 ml of an aqueous solution of the residue and sodium bicarbonate (0.22 g, 2.57 mmol) was added to 5.6 ml of an aqueous solution of S-methylisothiourea sulfate (0.48 g, 1.71 mmol) and 2N aqueous NaOH (0.86 ml, 1.71 mmol), followed by stirring at room temperature for 14 hours. The resulting solid was collected by filtration, washed with water, and dried. This solid was dissolved in 5.8 ml of methanol; 0.12 g of 10% Pd—C was added, followed by stirring in a hydrogen atmosphere for 1 hour. After the catalyst was filtered off, the filtrate was concentrated under reduced pressure. The residue was purified by CHP-20 column chromatography (H₂O→5% CH₃CN→10% CH₃CN) to yield (S,S)-4-{2-amino-3-(4-methoxyphenyl)propionyl}-3-(4-guanidinobutyl)-2-oxopiperazine-1-acetic acid. This intermediate (0.16 g, 0.36 mmol) and sodium bicarbonate (0.09 g, 1.07 mmol) were dissolved in 3.2 ml of H₂O and 1.6 ml of 1,4-dioxane; under stirring at room temperature, 4-amidinobenzoyl chloride hydrochloride (0.10 g, 0.46 mmol) was added. After being stirred for 1.5 hours, the reaction mixture was adjusted to pH 4 with 1N aqueous HCl and concentrated under reduced pressure. The residue was purified by CHP-20 column chromatography (H₂O→5% CH₃CN) to yield 0.16 g (27.3%) of the title compound as a colorless amorphous powder.

Optical rotation: $[\alpha]_D$ +62.7° (C=0.99, MeOH)
Elemental analysis (for $C_{29}H_{38}N_8O_6 \cdot HCl \cdot 3H_2O$ (685.176)):
Calculated: C, 50.84; H, 6.62; N, 16.35
Found: C, 50.76; H, 6.47; N, 16.11

Reference Example 22

(S)-4-(4-amidinobenzoylamino)acetyl-3-{3-(4-guanidinobutanoylamino)propyl}-2-oxopiperazine-1-acetic acid hydrochloride (S)-4-benzyloxycarbonylaminoacetyl-3-(3-(4-tert-butoxycarbonylaminobutanoylamino)propyl}-2-oxopiperazine-1-acetic acid as obtained in Reference Example 19 (0.33 g, 0.56 mmol) was dissolved in 6.6 ml of trifluoroacetic acid, followed by stirring at room temperature for 1 hour, after which the reaction mixture was concentrated under reduced pressure. 3.3 ml of an aqueous solution of the residue and sodium bicarbonate (0.14 g, 1.68 mmol) was added to 3.3 ml of an aqueous solution of S-methylisothiourea sulfate (0.93 g, 3.35 mmol) and 2N aqueous NaOH (1.68 ml, 3.35 mmol), followed by stirring at room temperature for 14 hours. The reaction mixture was concentrated under reduced pressure; the residue was purified by CHP-20 column chromatography (H₂O→5% CH₃CN→10% CH₃CN→15% CH₃CN) to yield (S)-[4-(benzyloxycarbonylamino)-acetyl-3-{3-(4-guanidinobutyrylamino)-propyl}-2-oxopiperazin-1-yl]-acetic acid. This intermediate was dissolved in 6.0 ml of methanol; 0.30 g of 10% Pd—C was added, followed by stirring in a hydrogen atmosphere for 1 hour. After the catalyst was filtered off, the filtrate was concentrated under reduced pressure. The residue and sodium bicarbonate (0.19 g, 2.23 mmol) was added to 6.0 ml of $H_2O$ and 3.0 ml of 1,4-dioxane; under stirring at room temperature, 4-amidinobenzoyl chloride hydrochloride (0.16 g, 0.73 mmol) was added. After being stirred for 1.0 hour, the reaction mixture was adjusted to pH 4 with 1N aqueous HCl and concentrated under reduced pressure. The residue was purified by CHP-20 column chromatography ($H_2O$) to yield 0.09 g (24.7%) of the title compound as a colorless amorphous powder.

Optical rotation: $[\alpha]_D$ +48.4° (C=0.96, $H_2O$)
Elemental analysis (for $C_{24}H_{35}N_9O_6 \cdot 2HCl \cdot 3.5H_2O$ (681.572)):
Calculated: C, 42.29; H, 6.51; N, 18.50
Found: C, 42.34; H, 6.59; N, 18.28

Reference Example 23

4-(N-benzyloxycarbonyl)glycyl-1-tert-butoxycarbonylmethyl-2-oxopiperazine-3-acetic acid 1.46 g of 4-(N-benzyloxycarbonyl)glycyl-1-tert-butoxycarbonylmethyl-2-oxopiperazine-3-acetic acid methyl ester was dissolved in a mixture of 5 ml of water and 5 ml of methanol; 190 mg of lithium hydroxide monohydrate was added at 0° C. over 5 minutes. After being stirred at 0° C. for 1 hour then at room temperature for 1 hour, the reaction mixture was adjusted to pH 7 with 5% aqueous potassium hydrogen sulfate; the methanol was removed by concentration under reduced pressure. After being adjusted to pH 3 with additional 5% aqueous potassium hydrogen sulfate, the residue was extracted with ethyl acetate. The extract was dried over anhydrous magnesium sulfate and concentrated under reduced pressure to yield 1.1 g of the title compound as a colorless oily substance.

NMR ($CDCl_3$) δ: 1.452 (9H, s), 2.80–4.65 (10H, m), 5.10 (2H, s), 5.82 (1H, m), 6.03 (1H, m), 7.33 (5H, s) IR ν max $cm^{-1}$: 3000, 1730, 1660, 1465, 1370, 1230, 1160

Reference Example 24

3-(4-amidinophenyl)aminocarbonylmethyl-4-(N-benzyloxycarbonyl)glycyl-2-oxopiperazine-1-acetic acid tert-butyl ester 820 mg of 4-(N-benzyloxycarbonyl)glycyl-1-tert-butoxycarbonylmethyl-2-oxopiperazine-3-acetic acid as obtained in Reference Example 9 and 370 mg of 4-aminobenzamidine dihydrochloride were dissolved in 5 ml of pyridine; 370 mg of dicyclohexylcarbodiimide and 10 mg of 4-dimethylaminopyridine were added at room temperature, followed by stirring at constant temperature for 24 hours. After the insoluble substances were filtered off, the filtrate was concentrated under reduced pressure; the resulting crude product was dissolved in 1% aqueous hydrochloric acid and subjected to CHP-20 column chromatography. The fraction eluted with 5% acetonitrile-water was freeze-dried to yield 550 mg of the title compound as a colorless powder.

NMR ($DMSO_{d-6}$) δ: 1.42 (9H, s), 2.83–4.44 (13H, m), 5.02 (2H, s), 7.34 (5H, s), 7.78–7.82 (4H, m), 9.03–9.25 (3H, m) IR ν max $cm^{-1}$: 3325, 1730, 1680, 1640, 1480, 1365, 1260, 1155

Reference Example 25

(S)-4-[N-(4-amidinobenzoyl)glycyl]-3-(4-amidinophenyl)-aminocarbonylmethyl-2-oxopiperazine-1-acetic acid 930 mg of 3-(4-amidinophenyl)aminocarbonylmethyl-4-(N-benzyloxycarbonyl)glycyl-2-oxopiperazine-1-acetic acid tert-butyl ester as obtained in Reference Example 12 was dissolved in 15 ml of methanol; 100 mg of 10% palladiumcarbon was added, followed by stirring in a hydrogen atmosphere for 1 hour. After the reduction catalyst was filtered off, the filtrate was concentrated under reduced pressure. To a solution of the resulting oily substance and 350 mg of sodium hydrogen carbonate in a mixture of 25 ml of water and 25 ml of dioxane, 307 mg of 4-amidinobenzoic acid was added over 5 minutes, while the solution was vigorously stirred at room temperature. After the reaction mixture was concentrated, the resulting crude product was dissolved in 5 ml of dichloromethane; 5 ml of trifluoroacetic acid was added at room temperature, followed by stirring for 1 hour. After the reaction mixture was concentrated under reduced pressure, the resulting crude product was purified by CHP-20 column chromatography to yield 490 mg of the title compound as a colorless powder.

Optical rotation: $[\alpha]_D^{23}$ +57.5° (C=0.9, $H_2O$)
Elemental analysis (for $C_{25}H_{28}N_8O_6 \cdot CF_3CO_2H \cdot 2.7H_2O$):
Calculated: C, 46.41; H, 4.96; N, 16.04
Found: C, 46.56; H, 4.80; N, 15.84

Reference Example 26

(S)-4-(4-Guanidinobenzoylamino)acetyl-3-[3-(4-guanidinobenzoylamino)]propyl-2-oxopiperazine-1-acetic acid hydrochloride In 4.9 ml of trifluoroacetic acid was dissolved 0.7 g of (S)-4-benzyloxycarbonylaminoacetyl-3-(3-t-butoxycarbonylamino)propyl-2-oxopiperazine-1-acetic acid t-butyl ester produced in Reference Example 2. The solution was stirred for one hour at room temperature. The reaction mixture was concentrated under reduced pressure, and then subjected to azeotropic distillation with toluene several times. The residue was subjected to a CHP-20 (Mitsubishi Chemical Industries, Ltd.) column chromatography. Fractions eluted with 20% acetonitrile/water were combined and concentrated to give (S)-4-benzyloxycarbonylaminoacetyl-3-(3-amino)propyl-2-oxopiperazine-1-acetic acid as a crude product. This crude product was dissolved in 12.0 ml of methanol, to which was added 250 mg of 10% Pd—C, and then the mixture was stirred for one hour under hydrogen atmosphere. The catalyst was filtered off, and the filtrate was concentrated under reduced pressure. The concentrate and 836 mg of sodium hydrogencarbonate were dissolved in a mixture of 7.0 ml of 1,4-dioxane and 14.0 ml of water. To the solution was added, while stirring at room temperature, 1.27 g of 4-quanidinobenzoic acid N-hydroxy-5-norbornene-2,3-dicarboxylic acid imidoester hydrochloride. The mixture was stirred for one hour, then pH of the reaction mixture was adjusted to 3 to 4 with 1N hydrochloric acid, followed by concentration under reduced pressure. The concentrate was subjected to CHP-20 column chromatography (eluted with 5% $CH_3CN/H_2O$). Relevant fractions were combined and freeze-dried to afford 0.48 g of the titled compound as a colorless amorphous powdery product.

Optical rotation: $[\alpha]_D^{20}$ +56.3° (C=1.017, $H_2O$)
Elemental analysis for $C_{27}H_{34}N_{10}O_6 \cdot 1.0HCl \cdot 3.5H_2O$:
Calculated: C, 46.72; H, 6.10; N, 20.18
Found: C, 46.56; H, 6.17; N, 20.05

Reference Example 27

(S)-3-(2-t-Butoxycarbonylamino)ethyl-2-oxopiperazine-1-acetic acid t-butyl ester oxalate In 200 ml of acetonitrile were dissolved 26 g of (S)-$N^2$-benzyloxycarbonyl-$N^4$-t-butoxycarbonyl-2,4-diaminobutanoic acid and 15.5 g of N-(2,2-dimethoxyethyl) glycine t-butyl ester. To the solution was added, while stirring at room temperature, 19 g of 1-ethyl-3-(3-dimethylaminopropyl)carbodiimide hydrochloride. The mixture was stirred for further two hours at the same temperature. The reaction mixture was then concentrated to leave an oily substance, which was dissolved in ethyl acetate. The solution was washed with a 5% aqueous solution of potassium hydrogensulfate and, then, with a saturated aqueous solution of sodium hydrogencarbonate. The solution was dried over anhydrous magnesium sulfate and concentrated under reduced pressure. The concentrate was dissolved in 500 ml of toluene, to which was added 1.4 g of p-toluenesulfonic acid. The mixture was stirred for 3 hours at 70° C., which was cooled to room temperature and washed with a saturated aqueous solution of sodium hydrogencarbonate. The mixture was dried over anhydrous magnesium sulfate, which was then concentrated under reduced pressure. The concentrate was dissolved in 500 ml of methanol, to which was added 10 g of 10% Pd—C. The mixture was stirred for 10 hours at room temperature under hydrogen atmosphere. The catalyst was filtered off. To the filtrate was added 6.4 g of oxalic acid, and the mixture was concentrated under reduced pressure to give a crude crystalline product. This crude product was recrystallized from methanol/ethyl acetate to afford 9.5 g of the titled compound as colorless crystals.

m.p. 165°–169° C.

Elemental analysis for $C_{17}H_{31}N_3O_5.(CO_2H)_2$:

Calculated: C, 51.00; H, 7.43; N, 9.39

Found: C, 50.78; H, 7.59; N, 9.14

Reference Example 28

(S)-4-(Benzyloxycarbonylamino)acetyl-3-(2-t-butoxycarbonylamino)ethyl-2-oxopiperazine-1-acetic acid t-butyl ester In 20 ml of dichloromethane was suspended 900 mg of (S)-3-(2-t-butoxycarbonylaminoethyl)-2-oxopiperazine-1-acetic acid t-butyl ester oxalate produced in Reference Example 27. To the suspension was added 20 ml of a saturated aqueous solution of sodium hydrogencarbonate, and the mixture was vigorously stirred for 10 minutes. The organic layer was separated and dried over anhydrous magnesium sulfate, to which were added 420 mg of N-benzyloxycarbonyl glycine and 500 mg of 1-ethyl-3-(3-dimethylaminopropyl)carbodiimide hydrochloride. The mixture was stirred for 2 hours at room temperature. The reaction mixture was concentrated under reduced pressure. The concentrate was dissolved in ethyl acetate, which was washed with 5% aqueous solution of potassium hydrogensulfate and a saturated aqueous solution of sodium hydrogencarbonate. The concentrate was dried over anhydrous magnesium sulfate, which was concentrated under reduced pressure. The concentrate was purified by means of a silica gel chromatography (eluent: ethyl acetate-hexane=3:1) to afford 1.05 g of the titled compound as a colorless oily product.

IR ν max cm$^{-1}$: 3450, 1705, 1655, 1640, 1500, 1450, 1360, 1240, 1160; NMR (CDCl$_3$) δ: 1.43 (9H, s), 1.46 (9H, s), 2.05-2.33 (1H, m), 2.73–2.95 (1, m), 3.15–4.20 (10H, m), 5.05 (1H, dd, J=3 Hz), 5.13 (2H, s), 5.30 (1H, brs), 5.83 (1H, brs), 7.36 (5H, s)

Reference Example 29

(S)-4-(4-Amidinobenzoylamino)acetyl-3-[2-(4-guanidinobenzoylamino)]ethyl-2-oxopiperazine-1-acetic acid hydrochloride In 5 ml of trifluoroacetic acid was dissolved 550 mg of (S)-4-(N-benzyloxycarbonylamino)acetyl-3-(2-t-butoxycarbonylamino)ethyl-2-oxopiperazine-1-acetic acid t-butyl ester produced in Reference Example 28. The solution was stirred for one hour at room temperature. The reaction mixture was concentrated to give an oily substance. This oily substance and 400 mg of sodium hydrogencarbonate were dissolved in a mixture of 25 ml of water and 25 ml of dioxane. To the solution was added, while stirring at room temperature, 250 mg of 4-guanidinobenzoyl chloride hydrochloride. The reaction mixture was adjusted to pH 7 with 1N HCl, to which was added 100 mg of 10% Pd—C. The mixture was stirred for one hour under hydrogen atmosphere. The catalyst was filtered off. To the filtrate were added 30 ml of dioxane and 400 mg of sodium hydrogencarbonate. To the mixture was added, while stirring vigorously, 230 mg of 4-amidinobenzoic acid hydrochloride. The reaction mixture was adjusted to pH 3 with 1N HCl, which was concentrated under reduced pressure to half of its initial volume. The concentrate was purified by means of a CHP-20 column (5% acetonitrile/water) to afford 250 mg of the titled compound as a colorless amorphous solid product.

Optical rotation: $[\alpha]_D^{20}$ +26.112° (C=0.450, MeOH)

Elemental analysis for $C_{26}H_{31}N_9O_6.HCl.5H_2O$:

Calculated: C, 45.12; H, 6.12; N, 18.21

Found: C, 45.61; H, 6.06; N, 18.22

Reference Example 30

(S)-3-[3-(4-Amidinobenzoylamino)]propyl-4-benzyloxycarbonylaminoacetyl-2-oxopiperazine-1-acetic acid In 6.8 ml of trifluoroacetic acid was dissolved 1.35 g of (S)-4-benzyloxycarbonylaminoacetyl-3-(3-t-butoxycarbonylaminopropyl)-2-oxopiperazine-1-acetic acid t-butyl ester produced in Reference Example 2. The solution was stirred for one hour at room temperature, which was then concentrated under reduced pressure. The concentrate was dissolved in a mixture of 20 ml of water and 10 ml of dioxane. To the solution were added 806 mg of sodium hydrogencarbonate and then 683 mg of 4-amidinobenzoyl chloride hydrochloride. The mixture was stirred vigorously for 30 minutes. The reaction mixture was concentrated to give a crude product, which was purified by means of a CHP-20 column (eluted with 20% acetonitrile/water) to afford 1.0 g of the titled compound as a colorless amorphous powdery product.

Optical rotation: $[\alpha]_D^{20}$ +106.6° (C=0.478, 0.1N HCl)

Elemental analysis for $C_{27}H_{32}N_6O_7.2H_2O$:

Calculated: C, 55.09; H, 6.16; N, 14.28

Found: C, 55.36; H, 6.10; N, 14.35

Reference Example 31

(S)-4-[4-(2-Aminoethyl)benzoylamino]acetyl-3-(3-[4-amidinobenzoylamino)]propyl-2-oxopiperazine-1-acetic acid trifluoroacetate In 20 ml of methanol was dissolved 300 mg of (S)-3-[3-(4-amidinobenzoylamino)]propyl-4-benzyloxycarbonylaminoacetyl-2-oxopiperazine-1-acetic acid produced in Reference Example 30. To the solution was added 120 mg of 10% Pd—C, and the mixture was stirred for one hour at room temperature in hydrogen streams. The catalyst was filtered off, and the filtrate was concentrated under reduced pressure to give an oily product, which was dissolved in 5 ml of dimethylformamide. To the solution was added 5 ml of activated-ester solution in dimethylformamide which was prepared from 94 mg of N-hydroxysuccinimide and 173 mg of 4-(2-t-butoxycarbonylaminoethyl)benzoic acid in the presence of 167 mg of 1-ethyl-3-(3-dimethylaminopropyl)carbodiimide hydrochloride. The mixture was stirred for two hours at room temperature. The reaction mixture was concentrated to give an oily product, which was dissolved in 7 ml of trifluoroacetic acid. The solution was stirred for one hour at room temperature. The reaction mixture was concentrated under reduced pressure to give a crude product, which was purified by means of a CHP-20 column (eluted with 10% acetonitrile/water) to afford 110 mg of the titled compound as a colorless amorphous powdery product.
Optical rotation: $[\alpha]_D^{20}$ +41.7° (C=1.018, MeOH)
Elemental analysis for $C_{28}H_{35}N_7O_6 \cdot 1.1CF_3CO_2H \cdot 4H_2O$:
Calculated: C, 47.53; H, 5.82; N, 12.85
Found: C, 47.64; H, 5.60; N, 12.72

Reference Example 32

(S,S)-4-[2-Benzyloxycarbonylamino-3-(4-methoxyphenyl) propionyl]-3-(3-tert-butoxycarbonylaminopropyl)-2-oxopiperazine-1-acetic acid tert-butyl ester In 50 ml of water was dissolved 4.2 g of (S)-3-(3-tert-butoxycarbonylamino)propyl-2-oxopiperazine-1-acetic acid tert-butyl ester·oxalate produced in Reference Example 5. To the solution was added 2.3 g of $NaHCO_3$. The mixture was subjected to extraction twice with 50 ml each portion of dichloromethane. The extract solution was dried ($NaSO_4$), followed by concentration under reduced pressure. To the concentrate was added 3 g of Z-Tyr(OMe)—OH, which was dissolved in 150 ml of dichloromethane. To the solution was added 1.92 g of WSC, which was stirred for two hours at room temperature. Dichloromethane was distilled off under reduced pressure, and the residue was subjected to extraction with ethyl acetate. The ethyl acetate layer was washed with a 3% aqueous solution of $KHSO_4$ and a saturated aqueous solution of $NaHCO_3$, which was dried ($Na_2SO_4$), followed by concentration under reduced pressure. The concentrate was purified by means of a silica gel chromatography (Hexane/AcOEt=1:2-AcOEt) to give 5.88 g of the title compound.

$^1$H-NMR (CDCl$_3$) δ: 1.35–2.10 (4H, m), 1.41 (9H, s), 1.46 (9H, s), 2.30 (1H, m), 2.80–3.85 (7H, m), 3.41 (1H, d, J=17.4 Hz), 3.78 (3H, s), 4.24 (1H, d, J=17.4 Hz), 4.75 (2H, m), 4.94 (1H, t, J=6.5 Hz), 5.10 (2H, q, J=12.4 Hz), 5.69 (1H, d, J=8.2 Hz), 6.80 (2H, d, J=8.6 Hz), 7.09 (2H, d, J=8.6 Hz), 7.35 (5H ,s)

Reference Example 33

(S,S)-3-(3-Aminopropyl)-4-[2-benzyloxycarbonylamino-3-(4-methoxyphenyl)propionyl]-2-oxopioperazine-1-acetic acid In 20 ml of toluene was suspended 5.7 g of (S,S)-4-[2-benzyloxycarbonylamino-3-(4-methoxyphenyl)propionyl]-3-(3-tert-butoxycarbonylaminopropyl)-2-oxopiperazine-1-acetic acid tert-butyl ester produced in Reference Example 32. The suspension was stirred under ice-cooling, to which was then added 20 ml of trifluoroacetic acid. The mixture was stirred for two hours at room temperature, to which was added toluene, followed by concentration under reduced pressure. The concentrate was dissolved in 30 ml of water, whose pH was adjusted to 5 with a conc. aqueous ammonia, followed by purification by means of an XAD-2 column chromatography (eluting with $H_2O \rightarrow 50\%CH_3CN$ water) to afford 4.3 g of the title compound.

$^1$H-NMR (CD$_3$OD) δ: 1.40–2.10 (4H, m), 2.32 (1H, m), 2.80–4.00 (7H, m), 3.16 (1H, d, J=16.5 Hz), 3.77 (3H, s), 4.61–4.85 (2H, m), 4.72 (1H, d, J=16.5 Hz), 5.05 (2H, q, J=12.3 Hz), 6.82 (2H, d, J=8.4 Hz), 7.11 (2H, d, J=8.4 Hz), 7.32 (5H, s)

Reference Example 34

(S,S)-4-[2-benzyloxycarbonylamino-3-(4-methoxyphenyl) propionyl]-3-(3-benzyloxycarbonylaminopropyl)-2-oxopiperazine-1-acetic acid In 100 ml of a 50% aqueous solution of dioxane was dissolved 3.8 g of (S,S)-3-(3-aminopropyl)-4-[2-benzyloxycarbonylamino-3-(4-methoxyphenyl)propionyl]-2-oxopiperazine- 1-acetic acid produced in Reference Example 33. To the solution was added 1.52 g of $NaHCO_3$, to which was added dropwise, under ice-cooling, 1.24 ml of Z-chloride. The mixture was stirred for 1.5 hour at room temperature. Dioxane was distilled off. To the residue was added a 3% aqueous solution of $KHSO_4$ to adjust the pH to 2. The mixture was subjected to extraction with ethyl acetate. The extract solution was washed with a saturated aqueous solution of $NaHCO_3$ and dried ($Na_2SO_4$), followed by concentration under reduced pressure. To the concentrate was added ether. The mixture was subjected to decantation twice to afford 4 g of the title compound.

$^1$H-NMR (CDCl$_3$) δ: 1.40–2.05 (4H, m), 2.22 (1H, m), 2.75 (9H, m), 3.74 (3H, s), 4.65–5.20 (6H, m), 5.52 (1H, t, J=5.5 Hz), 5.94 (1H, d, J=8.6 Hz), 6.78 (2H, d, J=8.6 Hz), 7.05 (2H, d, J=8.6 Hz), 7.31 (10H, s)

Reference Example 35

(S,S)-4-[2-Benzyloxycarbonylamino-3-(4-methoxyphenyl) propionyl]-3-(3-benzyloxycarbonylaminopropyl)-2-oxopiperazine-1-acetic acid tert-butyl ester In 50 ml of dichloromethane were dissolved 1.7 g of (S,S)-4-[2-benzyloxycarbonylamino-3-(4-methoxyphenyl) propionyl]-3-(3-benzyloxycarbonylaminopropyl)-2-oxopiperazine-1-acetic acid produced in Reference Example 34, 2 ml of tert-butanol and 1.6 g of 4-dimethylaminopyridine. To the solution was then added 0.6 g of WSC, and the mixture was stirred for 24 hours at room temperature. Dichloromethane was distilled off, and the residue was subjected to extraction with ethyl acetate. The ethyl acetate layer was washed with water and a saturated aqueous saline solution, which was then dried ($Na_2SO_4$), followed by concentration under reduced pressure. The concentrate was purified by means of a silica gel column chromatography (AcOEt), followed by crystallization from ether/hexane to afford 1.02 g of the title compound as colorless crystals.
m.p.: 138°–140° C.
Optical rotation: $[\alpha]_D^{20}$ +49.7° (C=0.431, MeOH)
Elemental analysis for $C_{39}H_{48}N_4O_9$(716.832):
Calculated: C, 65.35; H, 6.75; N, 7.82
Found : C, 65.17; H, 6.69; N, 7.91

Reference Example 36

(S,S)-4-[2-Benzyloxycarbonylamino-3-(4-methoxyphenyl) propionyl1-3-[3-(4-guanidinobenzoylamino)propyl]-2-oxopiperazine-1-acetic acid hydrochloride In 50 ml of a 50% aqueous solution of dioxane was dissolved 0.5 g of (S,S)-3-(3-aminopropyl)-4-[2-benzyloxycarbonylamino-3-(4-methoxyphenyl)propionyl1-2-oxopiperazine-1-acetic acid produced in Reference Example 35. To the solution was added 0.24 g of $NaHCO_3$, to which was then added 0.377 g of 4-guanidinobenzoic acid 3,5-dioxo-4-azatricyclo[5,2,1,0 2,6)deca-8-en-4-yl ester hydrochloride. The mixture was stirred for two hours at room temperature. The pH of the reaction mixture was adjusted to 3 with 1N-HCl, followed by distilling off dioxane. The residue was purified by means of a column chromatography (eluting with $H_2O \rightarrow 10\%$ aqueous solution of $CH_3CN \rightarrow$a 20% aqueous solution of $CH_3CN \rightarrow$a 50% aqueous solution of $CH_3CN$) to afford 0.43 g of the title compound.

$^1$H-NMR (CD$_3$OD) δ: 1.50–2.10 (4H, m), 2.45 (1H, m), 2.80–4.25 (9H, m), 3.77 (3H, s), 4.60–5.00 (2H, m), 5.00 (2H, s), 6.83 (2H, d, J=8.5 Hz), 7.13 (2H, d, J=8.5 Hz), 7.30 (5H, s), 7.35 (2H, d, J=8.5 Hz), 7.92 (2H, d, J=8.5 Hz)

Reference Example 37

(S,S)-3-(3-(4-Guanidinobenzoylamino)propyl]-4-[3-(4-methoxyphenyl)-2-]4-(5-trifluoromethyl[1,2,4]oxadiazol-3- ylamino)benzoylamino]propionyl]- 2-oxopiperazine-1-acetic acid hydrochloride

In 40 ml of methanol was dissolved (S,S)-4-[2-benzyloxycarbonylamino-3-(4-methoxyphenyl)propionyl]-3-[3-(4-guanidinobenzoylamino)propyl]-2-oxopiperazine-1-acetic acid hydrochloride produced in Reference Example 36. To the solution was added 0.2 g of 10% Pd—C. The mixture was subjected to catalytic reduction for two hours at room temperature. The catalyst was filtered off, and the filtrate was concentrated under reduced pressure, which was dissolved in 50 ml of a 50% aqueous solution of dioxane. To the solution was added dropwise, while maintaining the pH at alkaline side, a dioxane solution of the acid chloride prepared from 4-(5-trifluoromethyl-[1,2,4]oxadiazol-3-ylamino)benzoic acid and oxazolyl chloride. The mixture was stirred for 30 minutes at room temperature. The pH of the reaction mixture was adjusted to 3 with 1N-HCl, then the reaction mixture was concentrated to dryness. The concentrate was purified by means of a silica gel chromatography (AcOEt:AcOH:H$_2$O=8:1:1), to which was added ether to give 0.17 g of the title compound as a colorless powdery product.
Optical rotation: $[\alpha]_D^{20}$ +42.8° (C=0.94, DMSO)
Elemental analysis for C$_{37}$H$_{39}$N$_{10}$O$_8$F$_3$.HCl.0.1Et$_2$O (852.649):
Calculated: C, 52.68; H, 5.08; N, 16.43
Found: C, 52.62; H, 5.01; N, 16.58

Reference Example 38

(S,S)-4-[2-(4-Guanidinobenzoyl)amino-3-(4-methoxyphenyl)propionyl]-3-[3-(4-guanidinobenzoyl)aminopropyl]-2-oxopiperazine-1-acetic acid hydrochloride In 5 ml of methanol was dissolved 250 mg of (S,S)-3-(3-aminopropyl)-4-[2-benzyloxycarbonylamino-3-(4-methoxyphenyl)propionyl]-2-oxopiperazine-1-acetic acid produced in Reference Example 32. To the solution was added 100 mg of 10% Pd—C, and the mixture was stirred for one hour at room temperature in hydrogen atmosphere. The catalyst was filtered off, and the filtrate was concentrated under reduced pressure to leave an oily substance. The oily substance was dissolved in a mixture of 10 ml of dioxane and 10 ml of water. To the solution were added 210 mg of sodium hydrogencarbonate and 450 mg of 4-guanidinobenzoic acid 3,5-dioxo-4-azatricyclo[5,2,1,0 2,6]deca-8-en-4-ylester. The mixture was stirred for one hour at room temperature. The pH of the reaction mixture was adjusted to 3 with 1N HCl , then dioxane was distilled off under reduced pressure. The remaining aqueous solution was subjected to a CHP-20 column. The fraction eluted with 10% acetonitrile/water was freeze-dried to afford 130 mg of the title compound as an amorphous powdery product.
Elemental analysis for C$_{35}$H$_{42}$N$_{10}$O$_7$.2H$_2$O:
Calculated: C, 53.40; H, 6.02; N, 17.79
Found: C, 53.11; H, 5.86; N, 18.06

Reference Example 39

(S)-4-(4-Amidinobenzoylamino)acetyl-3-[2-(4-amidinobenzoylamino)]ethyl-2-oxopiperazine-1-acetic acid trifluoroacetate (S)-4-(Benzyloxycarbonylamino)acetyl-3-(2-t-butoxycarbonylamino)ethyl-2-oxopiperazine-1-acetic acid t-butyl ester produced in Reference Example 28 was subjected to substantially the same procedure as in Reference Example 3 and 4 to afford the titled compound as a colorless amorphous powdery product.
Optical rotation: $[\alpha]_D^{20}$ +30.299° (c=0.470,H$_2$O)
Elemental analysis for C$_{26}$H$_{30}$N$_8$O$_6$.CF$_3$CO$_2$H.3H$_2$O:
Calculated: C, 46.80; H, 5.19; N, 15.59
Found: C, 46.67; H, 4.99:N, 15.39

Reference Example 40

(S)-4-(4-Amidinobenzoylamino)acetyl-3-[2-(4-amidinophenylaminocarbonyl)ethyl]-2-oxopiperazine-1-acetic acid trifluoroacetate (S)-4-Benzyloxycarbonylaminoacetyl-1-t-butoxycarbonylmethyl-2-oxopiperazine-3-propanoic acid methyl ester was subjected to substantially the same procedure as in Reference Example 23, 24 and 25 to afford the titled compound as a colorless amorphous powdery product.
Optical rotation: $[\alpha]_D^{20}$ +59.625° (c=0.360,H$_2$O)
Elemental analysis for C$_{26}$H$_{30}$N$_8$O$_6$.CF$_3$CO$_2$H.4H$_2$O:
Calculated: C, 45.65; H, 5.34; N, 15.21
Found: C, 45.70; H, 5.10: N, 14.91

Reference Example 41

(S)-4-(4-Amidinobenzoylamino)acetyl-3-[3-(4-amidinophenylaminocarbonyl)propyl]-2-oxopiperazine-1-acetic acid trifluoroacetate Subjecting (S)-4-benzyloxycarbonylaminoacetyl-1-t-butoxy-carbonylmethyl-2-oxopiperazine-3-butanoic acid methyl ester to substantially the same procedure as in Reference Example 40, the titled compound will be obtained.

Reference Example 42

(S)-4-(4-Amidinobenzoylamino)acetyl-3-[4-(4-amidinophenylaminocarbonyl)butyl]-2-oxopiperazine-1-acetic acid trifluoroacetate Subjecting (S)-4-benzyloxycarbonylaminoacetyl-1-t-butoxy-carbonylmethyl-2-oxopiperazine-3-pentanoic acid methyl ester to substantially the same procedure as in Reference Example 40, the titled compound will be obtained.

What is claimed is:

1. A freeze-dried preparation for pharmaceutical use, comprising
    (i) a bioactive compound comprising an amidino group which may be substituted or unsubstituted, wherein said compound is not a peptide, and
    (ii) a disaccharide.

2. The freeze-dried preparation as claimed in claim 1, wherein said bioactive compound is a compound of the formula:

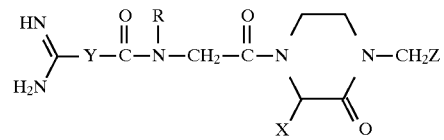

wherein R represents hydrogen or an alkyl group, X represents hydrogen or an optionally substituted alkyl group, Y represents a cyclic hydrocarbon group which may be bound through 1 to 2 atoms, and Z represents an optionally amidated or esterified carboxy group, or a pharmaceutically acceptable salt thereof.

3. The freeze-dried preparation as claimed in claim 1, wherein said bioactive compound is (S)-4-(4-amidinobenzoylglycyl)-3-methoxycarbonylmethyl-2-oxopiperazine-1-acetic acid, or a pharmaceutically acceptable salt thereof.

4. The freeze-dried preparation as claimed in claim 1, wherein said bioactive compound is (S)-4-(4-amidinobenzoyl)aminoacetyl-3-[3-(4-amidinobenzoyl)amino]propyl-2-oxopiperazine-1-acetic acid, or a pharmaceutically acceptable salt thereof.

5. The freeze-dried preparation as claimed in claim 1, wherein said bioactive compound is (S)-4-(4-guanidinobenzoyl)aminoacetyl-3-[3-(4-guanidinobenzoyl)amino]propyl-2-oxopiperazine-1-acetic acid, or a pharmaceutically acceptable salt thereof.

6. The freeze-dried preparation as claimed in claim 1, wherein the content of the disaccharide is from about 1 to about 1000 part by weight per 1 part by weight of the bioactive compound.

7. The freeze-dried preparation as claimed in claim 2, wherein:

R is a $C_{1-6}$ alkyl group;

X is a $C_{1-4}$ straight-chain alkyl group, which may unsubstituted or substituted with an optionally amidated or esterified carboxyl group, a phenyl group, or a group of the formula A—B—D, wherein A is an amino, amidino or guanidine group, B is a phenylene group and D is the group —CONH—;

Y is a saturated or unsaturated 5- or 6-membered cyclic hydrocarbon which may be bound through an imino group; and z is a carboxy group.

8. The freeze-dried preparation as claimed in claim 1, wherein said disaccharide is selected from the group consisting of maltose, cellobiose, gentiobiose, melibiose, lactose, turanose, sorbose, trehalose, isotrehalose, sucrose and isosaccharose.

9. The freeze-dried preparation as claimed in claim 8, wherein said disaccharide is selected from the group consisting of sucrose, lactose and maltose.

10. The freeze-dried preparation as claimed in claim 6, wherein the content of the disaccharide is from about 5 to about 500 parts by weight of disaccharide to 1 part by weight of the bioactive compound.

11. A sterile, injectable preparation comprising the freeze-dried preparation claimed in claim 1 and a pharmaceutically acceptable carrier.

12. A process for making a freeze-dried preparation for pharmaceutical use comprising a bioactive compound and a disaccharide comprising the steps of: dissolving a bioactive compound comprising an amidino group which may be substituted or unsubstituted and a disaccharide in a solvent selected from the group consisting of water and aqueous solvents, thereby forming an aqueous solution of said bioactive compound and said disaccharide; and freeze-drying said aqueous solution.

13. The freeze-dried preparation as claimed in claim 2, wherein X is a $C_{1-4}$ straight-chain alkyl group substituted with a group of the formula A—B—D, wherein A is an amino, amidino or guanidine group, B is a phenylene group, and D is the group —CONH—.

14. A process of stabilizing a bioactive compound comprising an amidino group which may be substituted or unsubstituted, comprising dissolving the bioactive compound and a disaccharide in a solvent selected from the group consisting of water and aqueous solvents, thereby forming an aqueous solution of said bioactive compound and said disaccharide, and freeze-drying said aqueous solution.

* * * * *

UNITED STATES PATENT AND TRADEMARK OFFICE
CERTIFICATE OF CORRECTION

PATENT NO. : 5,888,531
DATED : March 30, 1999
INVENTOR(S) : Motoya Ohshika et al.

It is certified that error appears in the above-identified patent and that said Letters Patent is hereby corrected as shown below:

Please note and correct on title page, [30] Foreign Application Priority Data should be cited -- Japanese Patent Application No. 165970; June 30, 1995 --.

<u>Column 20, claim 7,</u>
Line 13, delete "which may" and insert -- which may be --.

Signed and Sealed this

Sixteenth Day of October, 2001

Attest:

*Attesting Officer*

NICHOLAS P. GODICI
*Acting Director of the United States Patent and Trademark Office*